(12) United States Patent
Baril et al.

(10) Patent No.: US 11,051,834 B2
(45) Date of Patent: Jul. 6, 2021

(54) TISSUE SPECIMEN RETRIEVAL DEVICE

(71) Applicant: COVIDIEN LP, Mansfield, MA (US)

(72) Inventors: Jacob C. Baril, Norwalk, CT (US); Saumya Banerjee, Hamden, CT (US); Matthew A. Dinino, Newington, CT (US); Roy J. Pilletere, North Haven, CT (US); Justin J. Thomas, New Haven, CT (US); George S. Matta, Plainville, MA (US)

(73) Assignee: Covidien LP, Mansfield, MA (US)

( * ) Notice: Subject to any disclaimer, the term of this patent is extended or adjusted under 35 U.S.C. 154(b) by 142 days.

(21) Appl. No.: 16/415,715

(22) Filed: May 17, 2019

(65) Prior Publication Data
US 2020/0360031 A1 Nov. 19, 2020

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00287* (2013.01); *A61B 2017/2212* (2013.01)

(58) Field of Classification Search
CPC .......... A61B 17/221; A61B 2017/2212; A61B 2017/2215; A61B 2017/2217; A61B 2017/22035; A61B 2017/00287
See application file for complete search history.

(56) References Cited

U.S. PATENT DOCUMENTS

| | | | |
|---|---|---|---|
| 6,059,793 | A | 5/2000 | Pagedas |
| 6,156,055 | A | 12/2000 | Ravenscroft |
| 6,162,209 | A | 12/2000 | Gobron et al. |
| 6,171,317 | B1 | 1/2001 | Jackson et al. |
| 6,206,889 | B1 | 3/2001 | Bennardo |
| 6,224,612 | B1 | 5/2001 | Bates et al. |
| 6,228,095 | B1 | 5/2001 | Dennis |
| 6,248,113 | B1 | 6/2001 | Fina |
| 6,258,102 | B1 | 7/2001 | Pagedas |
| 6,264,663 | B1 | 7/2001 | Cano |
| 6,270,505 | B1 | 8/2001 | Yoshida et al. |
| 6,280,451 | B1 | 8/2001 | Bates et al. |
| 6,344,026 | B1 | 2/2002 | Burbank et al. |
| 6,350,266 | B1 | 2/2002 | White et al. |

(Continued)

*Primary Examiner* — Majid Jaialahmadi
(74) *Attorney, Agent, or Firm* — Carter, DeLuca & Farrell LLP

(57) ABSTRACT

A tissue specimen retrieval device includes a first shaft and a second shaft telescopically movable relative to the first shaft. The second shaft supports an end effector assembly at a distal end thereof and is movable relative to the first shaft between a retracted position, wherein the end effector assembly is disposed within the first shaft, and a deployed position, wherein the end effector assembly extends from the first shaft in an expanded configuration. The end effector assembly includes a bag brim having a wire support with first and second ends that operably engage the distal end of the second shaft. The bag brim is transitionable from a first collapsed configuration within the first shaft to an expanded configuration upon deployment therefrom. The wire support includes torsion springs disposed between the first and second ends that cooperate to facilitate expansion of the bag brim upon deployment from the first shaft.

14 Claims, 5 Drawing Sheets

(56) References Cited

U.S. PATENT DOCUMENTS

| | | | |
|---|---|---|---|
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2012/0046667 A1* | 2/2012 | Cherry ............ A61B 17/00234 606/113 |

\* cited by examiner

TISSUE SPECIMEN RETRIEVAL DEVICE

BACKGROUND

Technical Field

The present disclosure relates to tissue specimen retrieval from an internal body cavity and, more particularly, to tissue specimen retrieval devices and methods to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue specimen retrieval device that includes a first shaft and a second shaft telescopically movable relative to the first shaft. The second shaft supports an end effector assembly at a distal end thereof and is movable relative to the first shaft between a retracted position, wherein the end effector assembly is disposed within the first shaft, and a deployed position, wherein the end effector assembly extends distally from the first shaft in an expanded configuration.

The end effector assembly includes a bag brim having a wire support with first and second ends that operably engage the distal end of the second shaft. The bag brim is transitionable from a first collapsed configuration for disposition within the first shaft to an expanded, substantially circular configuration upon deployment from the first shaft. The wire support includes two or more torsion springs disposed between the first and second ends thereof. The at least two torsion springs cooperate to facilitate automatic expansion of the bag brim to the expanded configuration upon deployment thereof from within the first shaft.

In aspects according to the present disclosure, the two or more torsion springs are spaced at equal distances around the wire support. In other aspects according to the present disclosure, the wire support includes at least three torsion springs disposed therealong configured to facilitate automatic expansion of the bag brim upon deployment from within the first shaft. In still other aspects according to the present disclosure, the bag brim includes a second wire support having first and second ends that operably engage the distal end of the second shaft. The second wire support includes two or more torsion springs disposed between the first and second ends thereof. The two or more torsion springs cooperating to facilitate automatic expansion of the bag brim to the expanded configuration upon deployment thereof from within the first shaft.

In aspects according to the present disclosure, the two or more torsion springs of the first and second wire supports are disposed in substantial registration relative to one another along each respective wire support. In other aspects according to the present disclosure, the two or more torsion springs of the first and second wire supports are held in substantial registration with one another by a rivet. In yet other aspects according to the present disclosure, the bag brim includes a heat shrink tubing that encapsulates the two or more torsion springs and/or the rivet.

In aspects according to the present disclosure, the wire support of the bag brim is made from high yield stainless steel. Other types of materials may also be utilized, e.g., polymers, plastics, shape memory alloys, composite materials, surgical stainless steel, aluminum etc.

In accordance with another aspects of the present disclosure is a tissue specimen retrieval device that includes a first shaft and a second shaft telescopically movable relative to the first shaft. The second shaft supports an end effector assembly at a distal end thereof and is movable relative to the first shaft between a retracted position, wherein the end effector assembly is disposed within the first shaft, and a deployed position, wherein the end effector assembly extends distally from the first shaft in an expanded configuration.

The end effector assembly includes a bag brim having first and second wire supports each including first and second ends that operably engage the distal end of the second shaft. The bag brim is transitionable from a first collapsed configuration for disposition within the first shaft to an expanded configuration upon deployment from the first shaft. The wire supports each include two or more torsion springs disposed between each first and second end thereof. Each respective torsion spring of the two or more torsion springs of each wire support is disposed in substantial registration with the respective torsion spring of the other wire support and cooperates to form a corresponding number of dual torsion springs configured to facilitate automatic expansion of the bag brim to the expanded configuration upon deployment thereof from within the first shaft.

In aspects according to the present disclosure, the dual torsion springs are spaced at equal distances around the bag brim. In other aspects according to the present disclosure, the bag brim includes three or more dual torsion springs disposed therealong configured to facilitate automatic expansion of the bag brim upon deployment from within the first shaft.

In aspects according to the present disclosure, the two or more torsion springs of the first and second wire supports are held in substantial registration with one another by a rivet. In yet other aspects according to the present disclosure, the bag brim includes a heat shrink tubing that encapsulates each dual torsion spring. In still other aspects according to the present disclosure, the wire supports of the bag brim are made from high yield stainless steel. Other types of materials may also be utilized, e.g., polymers, plastics, shape memory alloys, composite materials, surgical stainless steel, aluminum etc.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
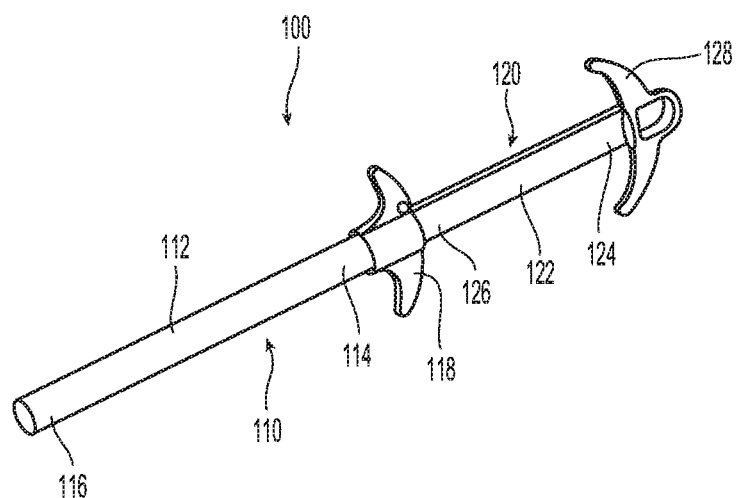
FIG. 1 is a perspective view of a tissue specimen retrieval device provided in accordance with aspects of the present disclosure, disposed in a retracted position.
Figure 2A:
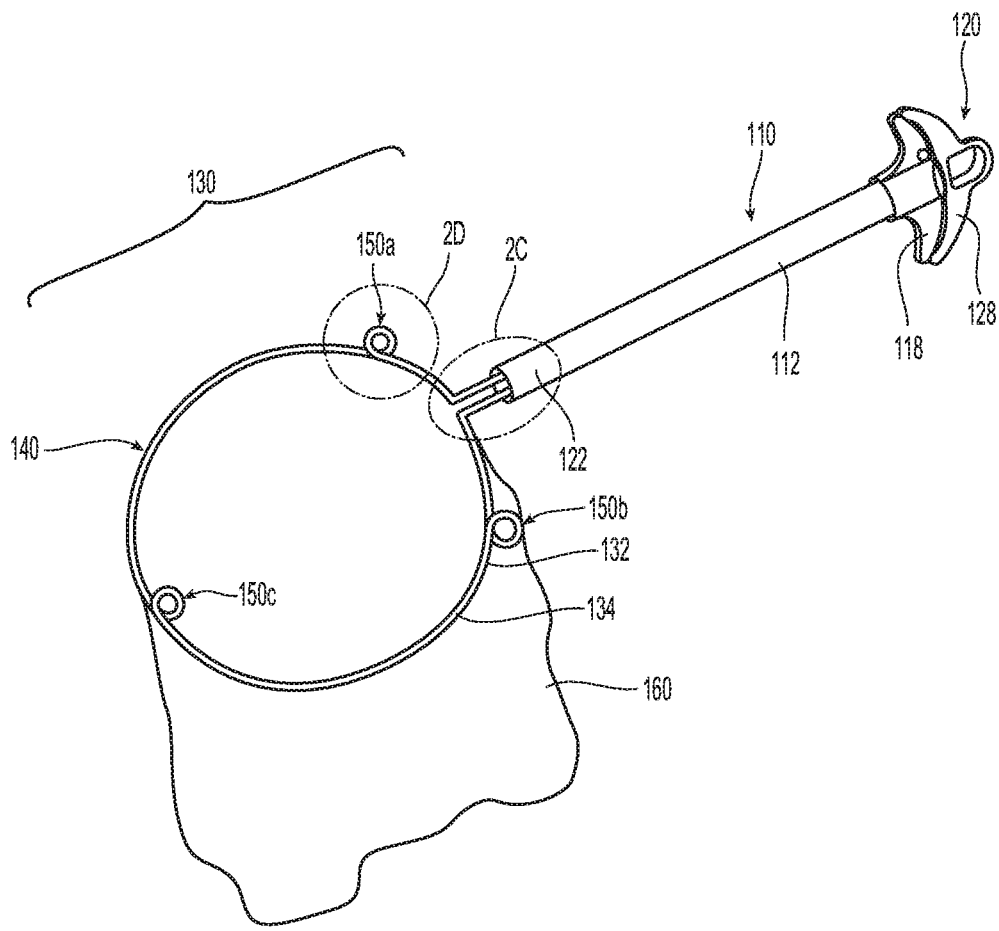
FIG. 2A is a perspective view of the tissue specimen retrieval device of FIG. 1, disposed in a deployed position showing a bag brim supporting a specimen bag.
Figure 2B:
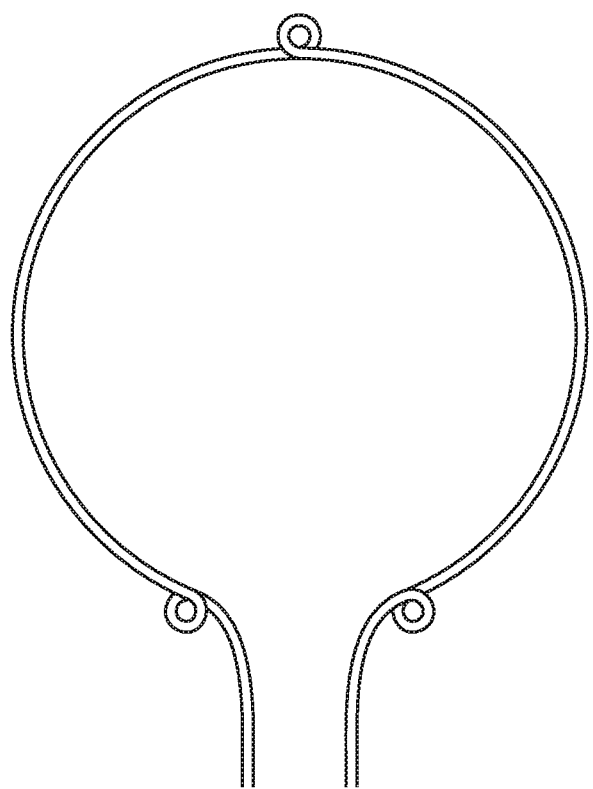
FIG. 2B is a top view of the bag brim of FIG. 2A.
Figure 2C:
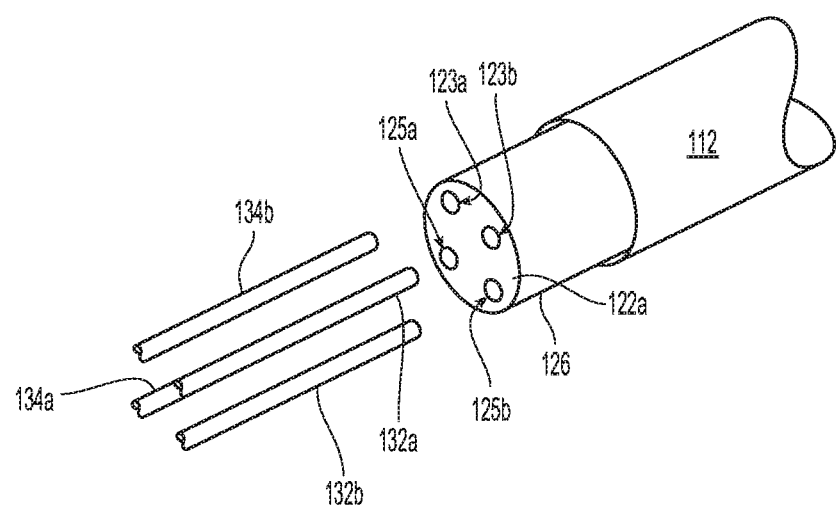
FIG. 2C is an enlarged view of the area of detail in FIG. 2A.
Figure 2D:
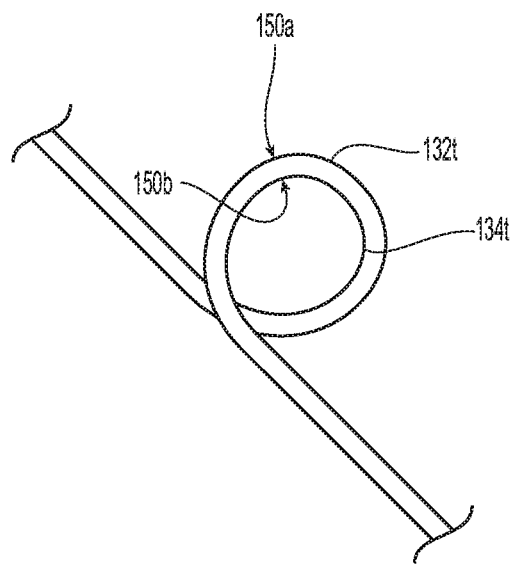
FIG. 2D is an enlarged view of the area of detail in FIG. 2A.
Figure 2E:
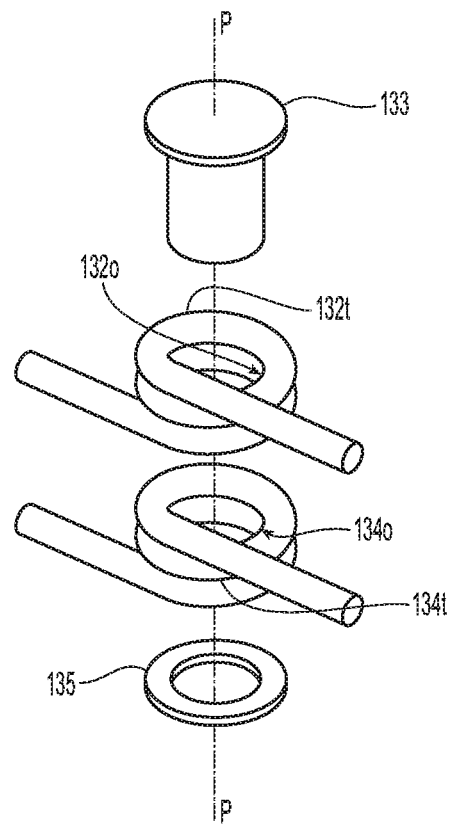
FIG. 2E is an enlarged view of two torsion springs along the bag brim joined by a rivet.
Figure 2F:
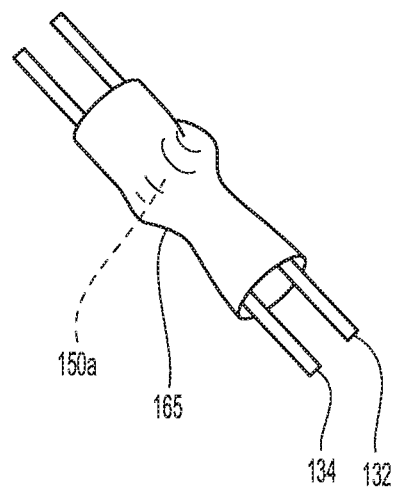
FIG. 2F is an enlarged view of the torsion spring of FIG. 2E with heat shrink tubing covering the torsion spring to prevent pitching.
Figure 2G:
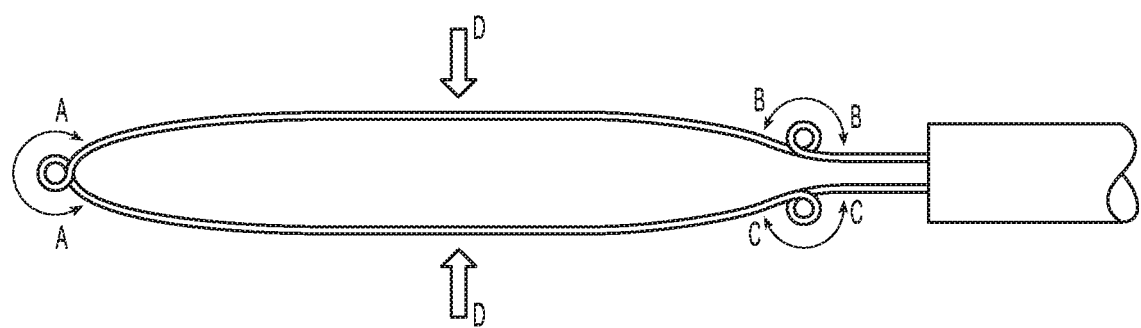
FIG. 2G is a top view of the bag brim of FIG. 2A shown in a compressed configuration for insertion within a shaft of the tissue specimen retrieval device.

Turning to FIGS. 1-2G, a tissue specimen retrieval device provided in accordance with the present disclosure is shown generally identified by reference numeral 100. Tissue specimen retrieval device 100 includes a first body 110, a second body 120, and an end effector assembly 130 including a bag brim 140 and a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2A), wherein end effector assembly 130 extends distally from first shaft 112 to deploy the bag brim 140 and specimen bag 160. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2A) to move tissue specimen retrieval device 100 from the retracted position (FIG. 1), wherein end effector assembly 130 is disposed within first shaft 112, to the deployed position (FIG. 2A), wherein end effector assembly 130 extends distally from first shaft 112.

Referring to FIGS. 2A-2G, end effector assembly 130, as noted above, is supported at distal end portion 126 of second shaft 122. End effector assembly 130, more specifically, includes bag brim 140 extending distally from distal end portion 126 of second shaft 122 and a specimen bag 160 supported on the bag brim 140. Bag brim 140 includes two substantially circular wire supports 132, 134 that extend from a distal face 122a of shaft 122. Bag brim 140 may be made from high yield stainless steel that may be heat treated after initial shaping. Other types of materials may also be utilized, e.g., polymers, plastics, shape memory alloys, composite materials, surgical stainless steel, aluminum etc.

More specifically and as best shown in FIG. 2C, wire support 132 includes free ends 132a and 132b that each operably engage a corresponding aperture 125a, 125b defined within the distal face 122a of the second shaft 122 (either selectively engage or are affixed therein) to form a ring-like support for supporting the specimen bag 160. Likewise, wire support 134 includes free ends 134a and 134b that each operably engage a corresponding aperture 123a, 123b defined within the distal face 122a of the second shaft 122 (either selectively engage or are affixed therein) to form a ring-like support for supporting the specimen bag 160 in conjunction with wire support 132. Distal face 122a may be configured to work with a single wire support, e.g., wire support 132, depending upon a particular purpose.

With continued reference to FIGS. 2A-2G, each wire support 132, 134 of bag brim 140 includes one or more twisted portions, e.g., twisted portion 132t, 134t, disposed between free ends 132a, 132b and 134a, 134b, respectively. Twisted portion 132t acts like a first torsion spring and twisted portion 134t acts like a second torsion spring, which, together act like a dual torsion spring, e.g., torsion spring 150a. Multiple torsion springs, e.g., 150a and 150b may be positioned along the wire support 140, e.g., at equal distances therealong. FIGS. 2A, 2B and 2G show three (3) dual torsion springs 150a, 150b and 150c utilized in connection with the bag brim 140 for supporting specimen bag 160. When used in this fashion, the three (3) dual torsion springs 150a, 150b and 150c cooperate to allow the specimen bag 160 to unfurl (FIG. 2B) quickly and easily when the bag brim 140 is deployed from the first shaft 112. Likewise the dual torsion springs 150a, 150b and 150c allow the specimen bag 160 to be collapsed (FIG. 2G) in a similar, albeit, reversed, fashion.

More particularly and as shown by the arrows in FIG. 2G, the positioning of each dual torsion spring 150a, 150b and 150c around the bag brim 140 facilitates automatic expansion of bag brim 140 and unfurling of the specimen bag 160 when the bag brim 140 is deployed from the first shaft 112 upon approximation of the first handle 118 proximally relative to the second handle 128. Moreover, the surgeon can collapse the bag brim 140 and specimen bag 160 by simply squeezing the bag brim 140 between respective the dual torsion springs 150a, 150c and 150b, 150c to collapse the bag brim 140 for reinsertion within first shaft 112.

Turning now to FIG. 2E, a rivet 133 may be utilized to secure the two twisted portions 132t, 134t together along the bag brim 140 to maintain alignment and to provide a common pivot axis P-P therethrough. During assembly, the rivet 133 is inserted through each opening 132o and 134o defined in respective twisted portions 132t, 134t and then compressed to align each twisted portion 132t, 134t along axis P-P. A rivet cap 135 may be utilized to secure the rivet 133 within openings 132o, 134o. Heat shrink tubing 165 (FIG. 2F) may be utilized over the dual torsion springs, e.g., dual torsion spring 150a, to reduce the chances of the dual torsion springs 150a pinching tissue or reduce possible specimen bag 160 tears.

Figure 3A:
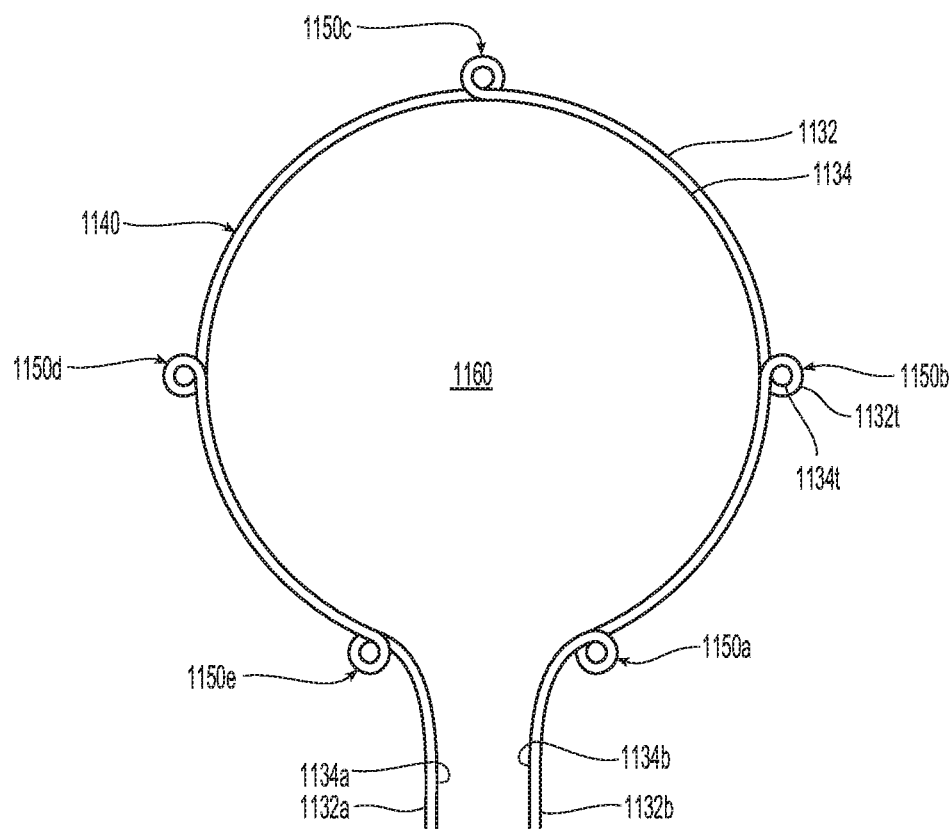
FIG. 3A is a top view of another embodiment of a bag brim with five dual torsion springs.
Figure 3B:
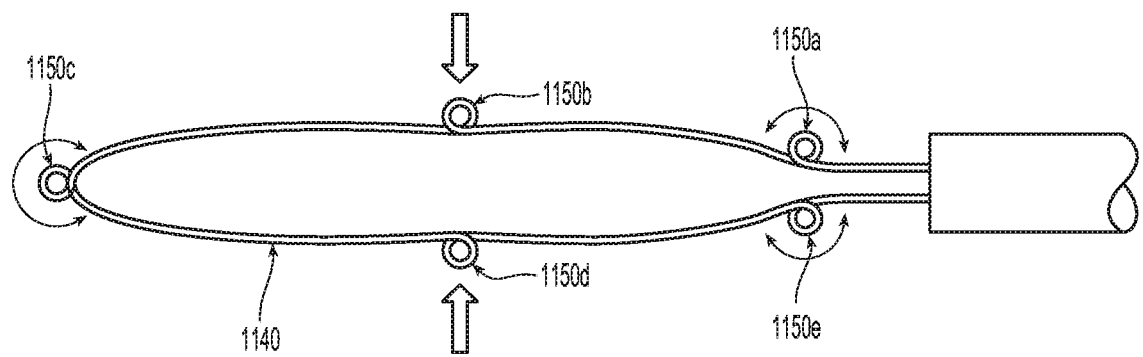
FIG. 3B is a top view of the bag brim of FIG. 3A shown in a compressed configuration for insertion within the shaft of the tissue specimen retrieval device.

Turning now to FIGS. 3A and 3B, another embodiment of the present tissue specimen retrieval device 1000 is shown. More particularly, tissue specimen retrieval device 1000 includes many of the same components as tissue specimen retrieval device 10 described above and for the purposes for brevity will only be discussed with reference to the differences between the two devices. Tissue specimen retrieval device 1000 includes end effector assembly 1130 having a bag brim 1140 extending distally from distal end portion 126 of second shaft 122 and a specimen bag 1160 supported on the bag brim 1140. Bag brim 1140 includes two substantially circular wire supports 1132, 1134 that extend from the distal face 122a of shaft 122. More specifically, wire support 1132 includes free ends 1132a and 1132b that each operably engage a corresponding aperture 125a, 125b (See FIG. 2C) defined within the distal face 122a of the second shaft 122 (either selectively engage or are affixed therein) to form a ring-like support for supporting the specimen bag 1160. Likewise, wire support 1134 includes free ends 1134a and 1134b that each operably engage a corresponding aperture 123a, 123b (See FIG. 2C) defined within the distal face 122a of the second shaft 122 (either selectively engage or are affixed therein) to form a ring-like support for supporting the specimen bag 1160 in conjunction with wire support 1132. Distal face 122a may be configured to work with a single wire support, e.g., wire support 1132, depending upon a particular purpose. In this instance, each dual torsion spring, e.g., dual torsion spring 1150a, would be part of a single wire support 1132 operably engaged to the distal face 122a.

With continued reference to FIGS. 3A and 3B, each wire support 1132, 1134 of bag brim 1140 includes one or more twisted portions, e.g., twisted portions 1132t, 1134t, disposed between free ends 1132a, 1132b and 1134a, 1134b, respectively. Twisted portion 1132t acts like a torsion spring and twisted portion 1134t acts like a second torsion spring, which, together act like a dual torsion spring, e.g., torsion spring 1150a. FIGS. 3A and 3B show five (5) dual torsion springs 1150a, 1150b, 1150c, 1150d and 1150e utilized in connection with the bag brim 1140 for supporting specimen bag 1160. When used in this fashion, the five (5) torsion springs 1150a, 1150b, 1150c, 1150d and 1150e cooperate to allow the specimen bag 1160 to unfurl (FIG. 3A) quickly and easily when the bag brim 1140 is deployed from the first shaft 112. Likewise the dual torsion springs 1150a, 1150b, 1150c, 1150d and 1150e allow the specimen bag 1160 to be collapsed (FIG. 3B) in a similar, albeit, reversed, fashion.

More particularly and as shown by the arrows in FIG. 3A, the positioning of each torsion spring 1150a, 1150b, 1150c, 1150d and 1150e around the bag brim 1140 facilitates automatic expansion of bag brim 1140 and unfurling of the specimen bag 1160 when the bag brim 1140 is deployed from the first shaft 112 upon approximation of the first handle 118 proximally relative to the second handle 128. Moreover, the surgeon can collapse the bag brim 1140 and specimen bag 1160 by simply squeezing the bag brim 1140 between respective the dual torsion springs, e.g., dual torsion springs 1150b, 1150d (See FIG. 3B), to collapse the bag brim 1140 for reinsertion within first shaft 112.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
    a first shaft;
    a second shaft telescopically movable relative to the first shaft, the second shaft supporting an end effector assembly at a distal end thereof and the second shaft is movable relative to the first shaft between a retracted position, wherein the end effector assembly is disposed within the first shaft, and a deployed position, wherein the end effector assembly extends distally from the first shaft in an expanded, substantially circular configuration, the end effector assembly including:
        a bag brim including first and second wire supports each having first and second ends that operably engage the distal end of the second shaft, the bag brim transitionable from a first collapsed configuration for disposition within the first shaft to the expanded, substantially circular configuration upon deployment from the first shaft, the first and second wire supports each including at least two torsion springs disposed between each of the first and second ends of their respective wire support of the first and second wire supports, the at least two torsion springs of the first and second wire supports cooperating to facilitate automatic expansion of the bag brim to the expanded, substantially circular configuration upon deployment thereof from within the first shaft.

2. The tissue specimen retrieval device according to claim 1 wherein the at least two torsion springs of the first and second wire supports are spaced at equal distances around their respective wire support of the first and second wire supports.

3. The tissue specimen retrieval device according to claim 1 wherein the at least two torsion sprinqs of the first and second wire supports each include at least three torsion springs disposed around their respective wire support of the first and second wire supports and are configured to facilitate automatic expansion of the bag brim upon deployment from within the first shaft.

4. The tissue specimen retrieval device according to claim 1 wherein the at least two torsion springs of the first and second wire supports are disposed in substantial registration relative to one another along each respective wire support of the first and second wire supports.

5. The tissue specimen retrieval device according to claim 4 wherein the at least two torsion springs of the first and second wire supports are held in substantial registration with one another by a rivet.

6. The tissue specimen retrieval device according to claim 5 wherein the bag brim includes a heat shrink tubing that encapsulates the at least two torsion springs of the first and second wire supports and the rivet.

7. The tissue specimen retrieval device according to claim 1 wherein the bag brim includes a heat shrink tubing that encapsulates the at least two torsion springs of the first and second wire supports.

8. The tissue specimen retrieval device according to claim 1 wherein the first and second wire supports of the bag brim are made from at least one of high yield stainless steel, one or more polymers, plastic, shape memory alloy, composite material, surgical stainless steel, or aluminum.

9. A tissue specimen retrieval device, comprising:
a first shaft;
a second shaft telescopically movable relative to the first shaft, the second shaft supporting an end effector assembly at a distal end thereof and the second shaft is movable relative to the first shaft between a retracted position, wherein the end effector assembly is disposed within the first shaft, and a deployed position, wherein the end effector assembly extends distally from the first shaft in an expanded configuration, the end effector assembly including:
a bag brim including first and second wire supports each having first and second ends that operably engage the distal end of the second shaft, the bag brim transitionable from a first collapsed configuration for disposition within the first shaft to the expanded configuration upon deployment from the first shaft, the first and second wire supports each including at least two torsion springs disposed between each of the first and second ends of their respective wire support of the first and second wire supports, each respective torsion spring of the at least two torsion springs of the first wire support are disposed in substantial registration with a respective torsion spring of the at least two torsion springs of the second wire support and cooperating to form a corresponding number of dual torsion springs configured to facilitate automatic expansion of the bag brim to the expanded configuration upon deployment thereof from within the first shaft.

10. The tissue specimen retrieval device according to claim 9 wherein the dual torsion springs are spaced at equal distances around the bag brim.

11. The tissue specimen retrieval device according to claim 9 wherein the dual torsion springs include at least three dual torsion springs disposed around the bag brim configured to facilitate automatic expansion of the bag brim upon deployment from within the first shaft.

12. The tissue specimen retrieval device according to claim 9 wherein the at least two torsion springs of the first and second wire supports are held in substantial registration with one another by a rivet.

13. The tissue specimen retrieval device according to claim 9 wherein the bag brim includes a heat shrink tubing encapsulating each of the dual torsion springs.

14. The tissue specimen retrieval device according to claim 9 wherein the first and second wire supports of the bag brim are made from at least one of high yield stainless steel, one or more polymers, plastic, shape memory alloy, composite material, surgical stainless steel, or aluminum.

\* \* \* \* \*